United States Patent
Statham et al.

(10) Patent No.: US 8,346,521 B2
(45) Date of Patent: Jan. 1, 2013

(54) METHOD OF DETERMINING THE FEASIBILITY OF A PROPOSED STRUCTURE ANALYSIS PROCESS

(75) Inventors: Peter John Statham, Bucks (GB); Charles Penman, High Wycombe (GB)

(73) Assignee: Oxford Instruments Nanotechnology Tools Limited, Oxon (GB)

( * ) Notice: Subject to any disclaimer, the term of this patent is extended or adjusted under 35 U.S.C. 154(b) by 779 days.

(21) Appl. No.: 12/300,963

(22) PCT Filed: May 16, 2007

(86) PCT No.: PCT/GB2007/001803
§ 371 (c)(1), (2), (4) Date: May 29, 2009

(87) PCT Pub. No.: WO2007/132243
PCT Pub. Date: Nov. 22, 2007

(65) Prior Publication Data
US 2010/0017172 A1    Jan. 21, 2010

(30) Foreign Application Priority Data
May 16, 2006 (GB) .................... 0609744.8

(51) Int. Cl.
*G06F 7/60* (2006.01)
*G06F 17/10* (2006.01)
*G06G 7/48* (2006.01)
*G06G 7/50* (2006.01)

(52) U.S. Cl. ......... 703/9; 703/2; 703/6; 378/45; 378/46; 378/47; 378/48; 378/49; 378/50; 378/51; 378/52; 378/53; 378/54; 378/55; 378/56

(58) Field of Classification Search .............. 378/45–56; 703/2, 6, 9
See application file for complete search history.

(56) References Cited

U.S. PATENT DOCUMENTS
5,687,210 A * 11/1997 Maitrejean et al. ............. 378/57
6,118,844 A * 9/2000 Fischer ........................... 378/48
(Continued)

FOREIGN PATENT DOCUMENTS
EP    1 736 759 A    12/2006

OTHER PUBLICATIONS

Weisbrod et al. "X-ray Induced Flourescence Spectrometry at Grazing Incidence for Quantitative Surface and Layer Analysis", Fresenius J Anal Chem (1991) 341:83-86.*

(Continued)

*Primary Examiner* — Shambhavi Patel
(74) *Attorney, Agent, or Firm* — Blank Rome LLP (57) ABSTRACT

A method of determining the feasibility of a proposed structure analysis process is disclosed. The process involved the electron beam excitation of x-rays from a multi-layered structure. The method comprises generating predicted x-ray data represents the x-ray excitation response of the multi-layered structure according to one or more sets of process conditions. The x-ray data are generated using structure data defining the structure and composition of the layers. The effects upon the x-ray data of changes to the structure data are then analyzed in accordance with one or more predetermined feasibility criteria, so as to determine the feasibility of performing the proposed structure analysis process upon the multi-layered structure.

35 Claims, 5 Drawing Sheets

U.S. PATENT DOCUMENTS

| | | | |
|---|---|---|---|
| 6,675,106 B1* | 1/2004 | Keenan et al. | 702/28 |
| 6,782,072 B2* | 8/2004 | Lin | 378/45 |
| 7,108,424 B2* | 9/2006 | Heumann et al. | 378/207 |
| 2003/0118148 A1* | 6/2003 | Kataoka et al. | 378/44 |
| 2004/0099805 A1* | 5/2004 | Ochiai et al. | 250/311 |
| 2006/0291619 A1* | 12/2006 | Statham | 378/45 |

OTHER PUBLICATIONS

Gauvin et al. "Win X-ray: A New Monte Carlo Program that Computes X-ray Spectra Obtained with a Scanning Electron Microscope", Microsc. Microanal. 12, 49-64, 2006.*

Petkov et al. "Atomic-scale structure of amorphous TiO2 by electron, X-ray diffraction and reverse Monte Carlo simulations", Journal of Non-Crystalline Solids 231 (1998) 17±30.*

Haimovich et al. "Estimating and Measuring Thickness of Thin Layers by Monte Carlo Simulation and Backscattered Electron Image Analysis", AMP Journal of Technology vol. 5 Jun. 1996.*

Newbury et al. "Simulation of electron-excited X-ray spectra with NIST-NIH Desktop Spectrum Analyzer (DTSA)", Surf. Interface Anal. 2005; 37: 1045-1053.*

Acosta et al. "Monte Carlo simulation of x-ray emission by kilovolt electron bombardment", J. Appl. Phys., vol. 83, No. 11, Jun. 1, 1998.*

Giersch et al. "ROSI-an object-oriented and parallel-computing Monte Carlo simulation for X-ray imaging", Nuclear Instruments and Methods in Physics Research A 509 (2003) 151-156.*

Duncumb et al. "Benefits of X-Ray Spectrum Simulation at Low Energies", Mikrochim, Act 138, 249-258 (2002).*

Lu et al. "SiO2 film thickness metrology by x-ray photoelectron spectroscopy", Appl. Phys. Lett. 71, 2764 (1997).*

Weisbrod et al. "X-ray induced fluorescence spectrometry at grazing incidence for quantitative surface and layer analysis", Fresenius J Anal Chem (1991) 341:83-86.*

Smekal et al. "Simulation of electron spectra for surface analysis (SESSA): a novel software tool for quantitative Auger-electron spectroscopy and X-ray photoelectron spectroscopy" Surf. Interface Anal. 2005; 37: 1059-1067.*

Womington et al. "Characterization of Structures from X-Ray Scattering Data Using Genetic Algorithms", Philosophical Transactions: Mathematical, Physical and Engineering Sciences, vol. 357,No. 1761, X-Ray Topography and Crystal Characterization (Oct. 15, 1999), pp. 2827-2848.*

Bonetto et al. "Optimization of parameters in electron probe microanalysis", X-Ray Spectrum. 2001; 30: 313-319.*

* cited by examiner

METHOD OF DETERMINING THE FEASIBILITY OF A PROPOSED STRUCTURE ANALYSIS PROCESS

CROSS-REFERENCE TO RELATED APPLICATIONS

The present application is a National Phase of PCT/GB2007/001803, filed May 16, 2007, which claims the benefit of Great Britain Application No. 0609744.8, filed May 16, 2006, the entire disclosures of which are incorporated by reference herein.

FIELD OF THE INVENTION

The present invention relates to a method of automatic optimisation of a proposed structure analysis process in which an electron beam is used to excite x-rays from a multi-layered structure under one or more process conditions.

BACKGROUND TO THE INVENTION

Figure 1:
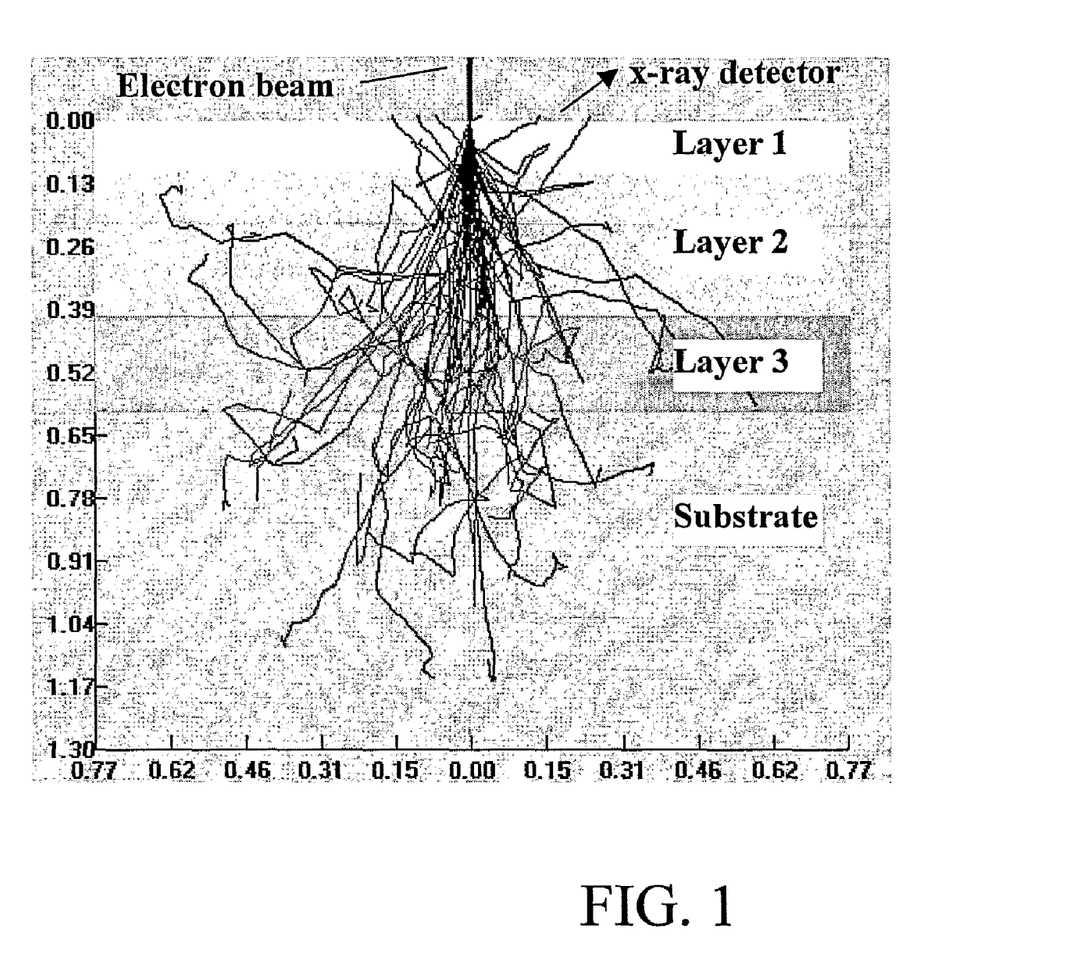
FIG. 1 shows the penetration of an electron beam into a multilayered sample.
Figure 2:
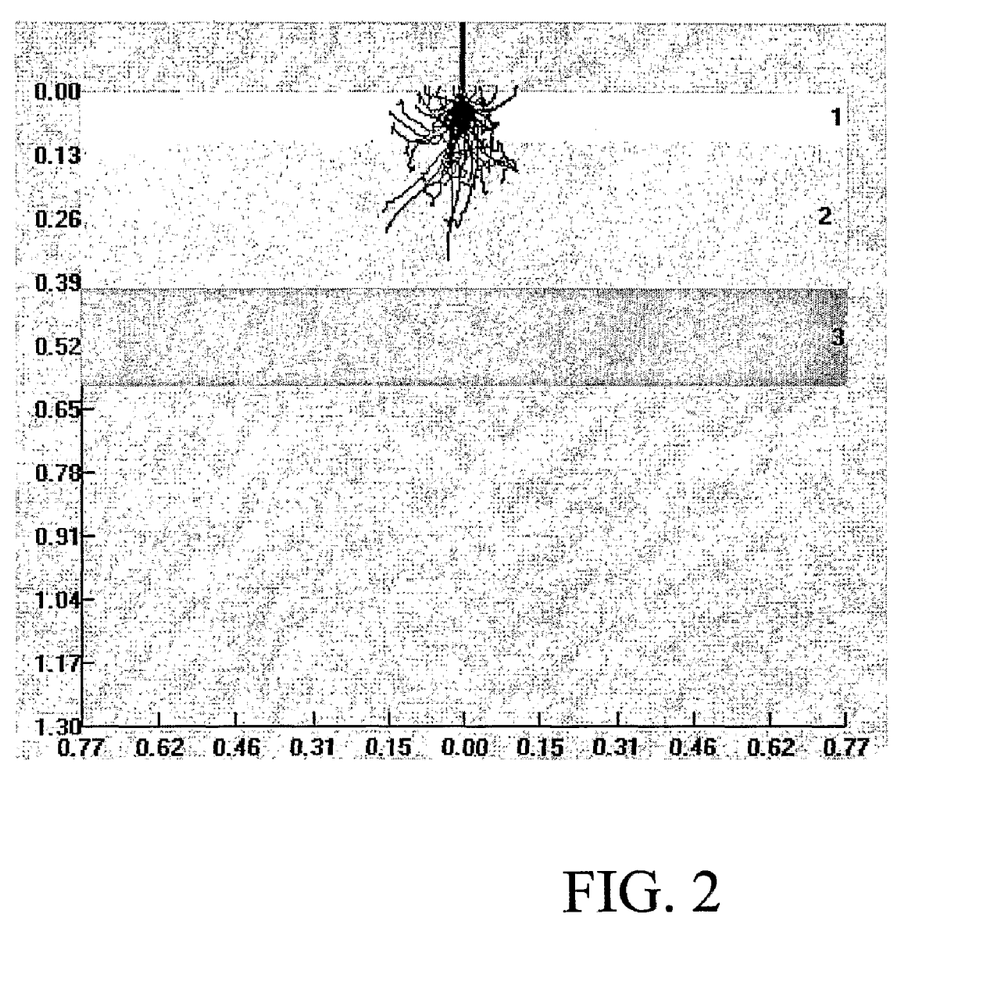
FIG. 2 shows the penetration of an electron beam having a lower beam energy than in FIG. 1.

One important method of analysing multiple thin layers on a substrate involves exposing a specimen to a beam of electrons and measuring the emitted x-ray spectrum. Provided the electron beam is sufficiently energetic to penetrate through the layers and reach the substrate, then characteristic x-rays are generated from elements in both the substrate and the various layers and these contribute to the total x-ray spectrum seen by an x-ray detector. FIG. 1 shows a typical situation where a 10 keV electron beam is incident on a layered sample with three layers of different thickness on a substrate. Many electron trajectories are shown and x-rays may be generated at any point along the electron trajectory as a result of ionisation of atoms. X-rays are emitted in all directions and if an x-ray detector is positioned above the sample, then x-rays emitted towards the detector will provide signals representative of the elements present in the regions excited by the electron beam. In the arrangement of FIG. 1, x-rays will emerge from all three layers and the substrate. In FIG. 2, the same sample is exposed to a lower energy electron beam. In this case, the electrons only penetrate to the top two layers so there will be no signal from the lowest layer and the substrate. In general, if a series of x-ray spectra are acquired at different incident electron beam energies, typically between 2 keV and 20 keV, then the corresponding spectra will exhibit characteristic x-ray peaks that vary according to the thicknesses and the compositions of the various layers, and indeed the substrate. Given a particular electron beam energy, the characteristic intensity for a particular element within a multi-layered sample can be expressed as a "k-ratio".

A "k-ratio" is the ratio of the x-ray intensity received for a particular element from the structure (counts per second recorded from a characteristic x-ray emission series such as K, L or M) to that obtained from a flat bulk specimen of pure element under the same experimental conditions. Taking this ratio avoids having to know the x-ray detector collection efficiency as a function of energy. By measuring a series of k-ratios, it is sometimes possible to deduce the thicknesses and compositions of the various layers in a multi-layer specimen.

If NE elements in total occur in one or more of the layers or in the substrate and there are NL layers with thickness $T_1$, $T_2$ ... $T_{NL}$, and layer L contains concentration $C_{Lj}$ of element j, and the substrate contains concentration $CS_j$ of element j then the predicted k-ratio for element i at incident electron beam energy $E_0$ can be written as:—

$$k_i = f_i(E_0, T_1, T_2, \ldots T_{NL}, C_{11}, C_{12}, \ldots C_{1NE}, C_{21}, C_{22} \ldots C_{2NE} \ldots C_{NL\,1}, C_{NL\,2}, \ldots C_{NL\,NE}, C_{S1}, C_{S2}, \ldots C_{S\,NE})$$

EQUATION 1 where $f_i$ is a non-linear function of the layer thicknesses and the compositions of the layers and substrate. Several equations of this form cover the measured element intensities at this one beam energy $E_0$. There may be more than one equation for a particular element if measurements are made on more than one emission series for this element (e.g. K or L or M emissions). Measurements may also be taken at further values of the beam energy and in general there will be M of these non-linear equations for k-ratios. The function in equation 1 typically involves integrations and non-linear functions and in general it is not possible to "invert" the set of equations and write down a formula that expresses the thickness or compositions for any one layer in terms of a set of measured k-ratios. Therefore, to determine a set of thicknesses and compositions ("layer variables") from a set of x-ray measurements, it is known to use a modelling approach where the parameters of the model are adjusted to find a set of $k_i$ that are a "best-fit" to the measured k-ratios (see for example, Chapter 15 in "Numerical Recipes in C", Second Edition, W.H. Press et al, Cambridge University Press 1999).

Thus, a computer program is used to make iterative guesses at the thickness and composition of the layers to find a set that is a close fit with the k-ratios measured from x-ray spectra (see for example, J. L. Pouchou. "X-ray microanalysis of stratified specimens", Analytica Chimica Acta, 283 (1993), 81-97. This procedure has been made available commercially in the software product "Stratagem" by SAMx, France). The computer program will make a test at each iteration to see if the guesses are not changing significantly between iterations, in which case "convergence" is achieved.

Unfortunately in some cases, it is impossible to find a best-fit set of thicknesses and compositions because the measured k-ratios do not reveal enough differences in intensity to resolve the source of the individual contributions to x-ray intensity. In this case, the computer program iterations will fail to converge on a unique solution. Such problems can sometimes be resolved by choosing different x-ray emission series, different beam energies or constraining the range of possible solutions by providing information on some of the thicknesses or compositions where this is known beforehand. Although there are some guidelines for the choice of beam energies and x-ray series (see for example, J. L. Pouchou, "X-ray Microanalysis of Thin Films and Coatings", Microchim. Acta 138, 133-152 (2002)), in general it is difficult to prove that a given type of sample can always be analysed successfully by this technique except by extensive experimentation in the hands of an expert. Existing software programs (such as "Stratagem") provide diagnostic tools such as curve plots of k-ratio vs layer thickness or k-ratio vs beam energy in order to assist the expert in making a choice of the best conditions for analysis. However, these tools do not provide any recommendations for analysis, particularly for a complex multi-layered specimen, and are not suitable for a person that does not have a good understanding of the physics involved.

The iterative procedure of the computer program begins with a set of starting values for the fitted parameters (that is the "unknowns") and the choice of starting "guesses" can affect whether the iteration will converge to the best solution for a given set of input data. Therefore, even when suitable conditions can be defined for the measurements and some prior knowledge is available, the procedure can still fail if the starting guesses for the fitted parameters are not suitable.

When an energy dispersive spectrometer is used to acquire an x-ray spectrum, the digitised spectrum effectively consists of a number of independent channels that each record counts for a small range of energies. To obtain peak intensities, the spectrum is processed mathematically to remove background and correct for any peak overlap. Each channel count in the original spectrum is subject to Poisson counting statistics and this will cause variation in the derived peak areas.

The physical theory for x-ray generation in layered specimens shows that a change in any one composition or thickness value will in general affect several of the observed x-ray intensities. Conversely, a change in one measured elemental intensity can influence several of the fitted parameters. In some situations, it is possible that some random perturbation of measured intensities together with the particular set of starting guesses for the fitted parameters will cause the program to sometimes succeed and sometimes fail to converge to a solution. In a quality control application where repeat measurements are taken to ensure thicknesses and/or compositions are within agreed tolerances, it is critical to ensure such failures are rare.

Even if convergence is always achieved, because of statistical variation each new set of measurements on the same specimen will give rise to a different set of results for thicknesses and composition. Using longer x-ray measurement times will in general reduce the fluctuation in measured k-ratios and this will in turn reduce the variation in thickness and composition estimates obtained by iteration. However, because of the complicated and mathematically non-linear nature of the problem, it is not possible to formulate equations to predict what precision can be achieved in the measured thicknesses or compositions.

A standard method to obtain estimates of reproducibility for such non-linear problems is to use Monte Carlo simulation (see "Numerical Recipes in C", Second Edition, W.H. Press et al, Cambridge University Press 1999, p 689). In this method, a set of results is first obtained from a set of input data. A set of random numbers representing the appropriate statistical distribution is added as a perturbation to the input data and the results found by iterative solution. These results will be slightly different from the results without the perturbations and the differences are recorded. This process is repeated many times with new sets of random numbers and the changing output results can be used to calculate the standard deviation for each result value as a consequence of counting statistics affecting the input data. For example, this sensitivity analysis approach has been used in the specialised field of x-ray fluorescence analysis where x-rays from an x-ray tube are used to excite an x-ray spectrum from the specimen (U.S. Pat. No. 6,118,844). In U.S. Pat. No. 6,118, 844 individual channel counts in the uncorrected x-ray data are subjected to counting statistic perturbations to predict the effect, after corrections for peak overlap, on the uncertainty in calculated layer thickness by the fluorescence method.

In the practical situation of a materials analyst being presented with a new type of thin film sample to be studied, experimental spectra usually have to be acquired from a similar but known sample to find the observed x-ray intensities from the various elements. Further experiments are usually then required to decide on the best set of measurement conditions, the element series to be measured, the fixed and variable parameters and the starting values. Thus it will be appreciated that the procedure to establish the feasibility of the electron beam analysis approach can be extremely time consuming and expensive. Furthermore, it requires considerable knowledge on the part of the operator There is therefore a desire to improve upon these known methods of determining the feasibility of performing electron beam x-ray analysis.

SUMMARY OF THE INVENTION

In accordance with the invention we provide a method of determining the feasibility of a proposed structure analysis process, said process comprising electron beam excitation of x-rays from a multi-layered structure in order to determine the structure and composition of the layers, the method comprising:— i) generating predicted x-ray data representing the x-ray excitation response of the multi-layered structure according to a first set of one or more process conditions, using structure data defining the structure and composition of the layers;

ii) analysing the effect upon the x-ray data of changes to the structure data in accordance with one or more predetermined feasibility criteria, wherein the said one or more predetermined feasibility criteria define whether or not it is possible for a structure solver, when given the x-ray data, to calculate output structure data defining the structure and composition of the multi-layered structure for x-ray data generated according to the first set of process conditions; and iii) automatically repeating steps (i) and (ii) using different process conditions in place of the first set of process conditions so as to determine under which process conditions, if any, the proposed structure analysis process can be used to determine the structure.

The invention can therefore be thought of as providing a simulation tool for determining whether a given multi-layer structure is "soluble" (for example in terms of determining the composition and/or thickness of each layer) by using an analysis technique based upon electron beam excitation of x-rays and to find the best conditions for that analysis. Typically such a multi-layered structure comprises at least one thin layer located upon a substrate. In principle a substrate is not required although normally this will be present. The invention may therefore be utilised in optimising the conditions for performing the analysis process and/or for determining the attainable precision or reproducibility in the "fitted" parameters estimated by this method.

Some layer variables will be known and fixed whereas some will be unknown and to be determined. In general it is impossible to guarantee that the iterative solution of equation 1 is possible for any specimen and for any selection of starting values for the unknown variables. However, if typical values are provided for the unknowns, then this provides enough information to define a hypothetical specimen structure that is typical of what is to be analysed. It is then possible to determine if the problem can be solved reliably with good starting guesses for the unknown variables. If the problem cannot be solved even with good starting guesses, then it cannot be solved in general and new set of process conditions needs to be selected.

Typically the x-ray data are generated using a predictor model as a function of the elemental composition and layer thickness of each layer in the multi-layered structure. Thus the predictor model may be used to generate x-ray data representing the characteristic x-ray intensity response for a particular element within the multi-layered structure. X-ray data for the structure as a whole can therefore be built up in this way by calculating the characteristic x-ray intensity response for each element. Thus, the predictor model ("thin film model") can always predict k-ratios in the 'forward' direction as shown by equation 1 provided thicknesses and concentrations ("layer variables") are defined for all layers.

In one method, in step (i) the structure data is defined as nominal structure data in terms of compositions and layer thicknesses for each layer, the nominal structure data producing corresponding nominal x-ray data and wherein, in step (ii), the x-ray data is modified and input, together with the nominal structure data, into a structure solver adapted to iteratively change the composition and thickness of each layer of the multi-layer structure to see the effect on the predicted x-ray data and find values that match the input x-ray data and thus produce output structure data that is consistent with the input x-ray data. As will be appreciated, in each of the methods described herein, the structure solver preferably applies equation 1 in search of a solution.

Preferably the effects of modifications to the x-ray data are then analysed by comparing the output structure data with the nominal structure data in accordance with a feasibility criterion. For example, the feasibility criterion is met if, for every modification to the input x-ray data, the structure solver produces a unique set of output structure data having corresponding x-ray data that is substantially identical to the nominal x-ray data. By way of further explanation of this method, if x-ray data are provided as k-ratios as inputs to the iterative procedure and the starting values for the unknowns are set to the values corresponding to the hypothetical specimen, then equation 1 will predict k-ratios identical to the starting values and the iteration will converge immediately. If just one of the k-ratios, $K_j$, is incremented by a small amount (say 1%) and the other k-ratios are unchanged, then when the iterative solution is attempted, the k-ratios will agree with equation 1 except for $K_j$. Provided the change in $K_j$ is sufficiently large, then the test for convergence will fail and the iterative procedure will have to perform an iteration and make an adjustment to the unknown values. This will change the prediction of k-ratios and may lead to further iterations. If the iterations fail to converge, then the problem is clearly unstable. However, if they do converge to a solution, then the change delta-$T_i$ from the ideal starting value for each unknown layer variable $T_i$ for a known change delta-$K_j$ in the jth k-ratio is recorded as $dT_i/dK_j$. This procedure is repeated for different $K_j$. If convergence is achieved for all $K_j$ then this suggests that the computer program embodying the method can deal with this problem.

If an estimate of the standard deviation, $\sigma_i$, in the measured $K_j$ is available, and the statistical fluctuations in all $K_j$ are independent, then the variance, $V_i$, in the calculated layer variable $T_i$ can be estimated as the sum of $((dT_i/dK_j)^2 \cdot \sigma_i^2)$ for all j. Furthermore, systematic errors can occur in measured $K_j$. For example, if the beam current increases during the acquisition of an x-ray spectrum, then all $K_j$ derived from this spectrum will be increased in the same proportion. If an estimate of the systematic error, $e_i$, in the measure $K_j$ is available, then the error in the calculated variable $T_i$ can be estimated as the sum of $((dT_i/dK_j) \cdot e_j)$ for all j. A figure of merit can be computed for each source of error. For example, in the case of statistical errors, the maximum relative standard deviation in $T_i$, that is square root of $(V_i/T_i^2)$, gives the "worst case" relative error and a low value for this figure of merit would be desirable. Alternatively, the average relative error for all $T_i$ or the relative error for a specific layer variable can be chosen for the figure of merit. Similar figures of merit can be computed for errors due to systematic causes such as beam current variation.

Thus, if a typical specimen structure can be defined, then for one set of experimental conditions, in particular the beam energy, the possibility of solving the problem can be tested and one or more figures of merit can be computed to measure the effect of various potential sources of error on the results. If this procedure is repeated at several candidate experimental conditions, then the best set of conditions can be found that minimises the effect of one or more sources of error. If one source of error is likely to dominate, then the conditions that minimise the figure of merit for that error source is appropriate. Alternatively, if realistic values for, $\sigma_i$ and $e_i$ are available, then some combination of the related figures of merit can be used, such as the maximum of both figures of merit, to find the experimental conditions that are optimal.

In an alternative approach, modifications of the structure data which are input into the structure solver can be made to determine the feasibility. In this case, in step (i) the structure data is defined as nominal structure data comprising compositions and layer thicknesses for each layer, the nominal structure data producing corresponding nominal x-ray data and wherein, in step (ii), the structure data is modified and input as starting guesses, together with the nominal x-ray data, into a structure solver adapted to iteratively calculate the composition and thickness of each layer of the multi-layer structure as output structure data using these starting guesses. The structure solver may therefore calculate x-ray data for the modified structure data and compare the modified x-ray data with the nominal x-ray data. Preferably the effects of the modification to the structure data are analysed by comparing the x-ray data generated for the modifications in the structure data with the nominal x-ray data and comparing the results of the comparison with a feasibility criterion. The feasibility criterion may be deemed met if a unique set of output structure data is found which produces corresponding predicted x-ray data that is substantially identical to the nominal x-ray data and is substantially independent of the modifications applied to the structure data.

In another alternative method, a Monte Carlo method is used wherein changes to nominal x-ray data generated from nominal structure data are produced by applying statistical distributions to the nominal x-ray data so as to produce a plurality of sets of x-ray data having a collective statistical distribution equivalent to that expected from performing the x-ray excitation experimentally. Thus in step (ii), each set of x-ray data may be entered, together with the nominal structure data, into an iterative structure solver for generating output structure data. In this case the process may be deemed feasible if, for every modification to the x-ray data the structure solver produces a unique set of output structure data having corresponding x-ray data that is substantially identical to the nominal x-ray data. Therefore, rather than consider the effect of small changes in each $K_i$ individually, it is possible to use a "Monte Carlo" approach where the expected standard deviations $\sigma_i$ are used to generate a randomised set of $K_j$ that are then used as input to the iterative procedure. If the iterative procedure converges on a solution, it will find values for the unknown layer variables that will be slightly different from the typical values used in equation 1. By repeating this procedure many times with fresh sets of random numbers, the iterative procedure will be tested many times and the standard deviation in the determined layer variables can be calculated from the many sets of results that effectively simulate many real experiments.

In this procedure, it is not necessary to calculate $dT_i/dK_j$ but does require much more computation to obtain estimates of the variations in determined layer variables. Sources of variation such as beam current can be incorporated by using another random number to calculate the scale factor to apply to all k-ratios obtained from a particular spectrum. If at any time, the iterative procedure fails to converge, then this particular set of conditions (e.g. beam energy) is clearly unsuitable for analysis and a new set of conditions should be investigated immediately.

Another alternative method of performing the invention comprises in step (i) generating one or more sets of predicted spectral data, each set representing the x-ray excitation response of the structure according to a respective one of the said process conditions and x-ray data are derived from the predicted spectral data wherein step (ii) comprises calculating output structure data for each set of process conditions, using x-ray data derived from each generated set of spectral data and nominal structure data. This method preferably uses a predictor model to generate numerous sets of spectral data for analysis by a structure solver.

In practice, the standard deviation in measured k-ratios will depend on the process conditions and can be calculated from physical theory for the typical specimen structure under consideration. Where k-ratios are determined from spectral data, the spectral data can be predicted according to a set of process conditions. Besides electron beam energy, such process conditions may include data concerning the type of physical apparatus used and the experimental conditions used, such as for example the acquisition time used for obtaining the spectral data. Examples of information used to predict the spectral data include the incident beam keV, the beam current, the solid angle for collection of x-rays, the take-off-angle for the emergent x-rays, the tilt of the specimen surface and spectrometer adjustable parameters (such as resolution and acquisition time). It is also necessary in this case to specify the particular elements and line series for which the spectral data are to be generated.

The form that the spectral data takes is also dependent upon the technique used to generate the spectral data. Typically it will depend upon the format required as an input for the calculations. The spectral data may therefore comprise predicted x-ray intensity data for example in the form of k-ratios as described earlier. In order to generate such k-ratios the method preferably further comprises generating elemental spectral data for pure elements and using the elemental spectral data in the generation of the x-ray data. Typically this involves dividing the "structure" x-ray data values by the elemental x-ray data values.

The "feasibility" of the structure analysis process is not limited to mean whether or not it is possible for the analysis process to arrive at the fitted parameters at all, but also in the sense of whether the fitted parameters arrived at have a sufficient level of reproducibility or accuracy. In making a feasibility determination it is therefore important to model the x-ray emission from the multi-layered structure to a sufficient level of accuracy. Real life x-ray excitation involves the probabilistic effects of counting statistics. Preferably therefore, for each data set (according to the conditions selected), the method further comprises running the iterative solution procedure a number of times, so as to simulate the effects of Poisson counting statistics within each data set by adding random numbers to the spectral data. This effectively simulates the effect of performing a practical analysis experiment a number of times.

Another technique that can be used to take the counting statistics into account is to perform calculations so as to predict the statistical distribution of x-ray peak areas due to Poisson counting statistics and then to apply the statistical distribution to the spectral data. For example, the effective $\sigma_i$ for each k-ratio can be calculated and used in the Monte Carlo approach described above, rather than simulating many spectra with counting statistics and processing each one to obtain a peak area.

Since there are often fluctuations in the electron beam intensity generated by practical electron beam generation apparatus, this can be taken into account by performing the method with different sets of processing conditions representing the electron beam intensity fluctuations. This can be effected for example by applying a probabilistic distribution to a nominal electron beam intensity for each simulated spectrum. This can also be achieved by adding the relative variance due to beam current fluctuations in quadrature with the relative variance due to counting statistics (as described later).

In some cases it may also be recognised that there are systematic errors within the processing of spectral data obtained from practical apparatus. The present invention can also be used to monitor the effects of such errors by modelling such systematic errors into the spectral data. The iterative solution procedure may be repeated a number of times in investigating the effects of these systematic errors in the spectrum processing upon the fitted parameters. This can also be achieved by adding the potential relative variance due to spectrum processing errors in quadrature with the relative variance due to counting statistics.

The results of the iterative solution procedure are typically a value for each fitted parameter. Such a value is normally a numerical value although it could also be a selection of particular data from a group of data. For example such data might represent further information about the type of multi-layered structure. Typically each fitted parameter is a composition (such as the amount of a particular element) or a layer thickness. When multiple fitted parameters are to be determined for a specimen, they may comprise different "types" of parameters, such as a mixture of composition and thickness parameters.

Whilst various parameters may be modified in the generation of the spectral data such as the process conditions, electron beam energies and so on, it will be appreciated that the program that drives the iterative solution procedure typically also includes a number of parameters which may be selected and thereby influence the feasibility of performing the analysis process. For example the "fitted" parameters which are to be determined may begin as undefined values in some calculation models. However, in certain types of model, such as iterative models as an example, typically starting values are provided for the "fitted" parameters and these are modified as the calculation proceeds so as to converge upon a single solution for each fitted parameter. The structure parameters used may likewise be modified. Typically the structure parameters define certain aspects of the multilayered structure, including information that is known about certain layers, for example the number of layers, the thickness of particular layers, the partial or total composition of particular layers and so on. The iterative solution procedure may therefore be repeated a number of times for each set whilst varying the structure parameters used in the calculation.

The analysis typically further comprises calculating a statistical distribution of the output fitted parameters. This analysis may be performed for the data within each set (for example where numerous spectra are produced due to counting statistics), for results due to the different starting parameters or for sets (due to the different experimental conditions selected for each set), or indeed a combination of one or more of these.

Typically the method further comprises calculating a standard deviation for each estimated fitted parameter as a measure of achievable precision for the analysis process. This is advantageous since one goal of the method in a practical implementation is to achieve a predetermined level of precision for a predetermined total measurement time.

Whilst the invention is limited to x-ray excitation using electron beams, the invention does include proposed structure analysis processes in terms of energy dispersive apparatus (EDS) and wavelength dispersive apparatus (WDS). Each of these may be considered as spectral data.

Since the purpose of the invention is to determine the feasibility of a proposed analysis process, the proposed process will not be feasible to use if the calculations are unable to produce meaningful results for the fitted parameters. This will be the case if the method is unable to produce single solutions for the fitted parameters. The data (such as parameters and conditions data) which cause such failures are typically recorded for later analysis. Where there is a failure to produce single solutions, the method preferably further comprises selecting new conditions and repeating the method using spectral data generated according to the new conditions. The method therefore explores other conditions which may produce meaningful results for the fitted parameters.

The invention therefore allows the feasibility of a proposed structure analysis process to be investigated without the need for expensive and lengthy practical investigations. This is extremely useful in commercial structure analysis processes, for example where products are produced containing multi-layered structures and automatic electron beam x-ray excitation analysis apparatus is provided for quality control purposes. The invention therefore allows the feasibility of a particular process to be investigated, this process having certain associated conditions and parameters, for all likely variations in the products (multi-layered structures) to be analysed. If a certain proposed analysis process having an associated set of conditions and parameters is deemed unable to converge upon a solution, then the modification of the conditions and/or parameters according to the method can allow a different proposed analysis process to be selected. If the desired precision cannot be achieved under any conditions, this will save wasted time and allow alternative characterisation methods to be sought.

We have further realised that it is possible to perform the method of the invention by considering whether it is mathematically possible to find unique values of the unknown parameters. Even if it is possible in theory, the particular iterative solution procedure used to implement the method may not succeed although this does provide an incentive to improve the iterative solution procedure.

As mentioned earlier, step (ii) may comprise analysing the response of the predictor model to small changes in the layer thickness and/or composition within the structure data. The behaviour of the predictor model may be analysed as an approximated series expansion for changes from the nominal values. For example the behaviour of the predictor model may be represented as a matrix equation, wherein x-ray data output from the predictor are represented as a vector of M values, wherein unknown layer thicknesses and/or compositions are represented as a vector of N variables, and wherein the partial derivatives relating the outputs to the layer thicknesses or compositions are represented as an M by N dimension Jacobian matrix. An analysis may therefore be performed to find if there is always a unique combination of small changes to unknown layer thicknesses and concentrations that can produce an arbitrary set of changes to the nominal x-ray data. One particular approach is that of singular value decomposition (SVD). Using such a technique the method may further comprise calculating the condition number representing the degree of solubility of the matrix equation for the layer thicknesses or compositions. This condition number may be compared with a threshold so as to comprise a feasibility criterion.

By way of further explanation, there are many methods of finding solutions to sets of non-linear equations and many variants of iterative solution procedures. Some algorithms may converge successfully whereas other algorithms may fail, even though identical equations are used like equation 1 to predict x-ray intensities Out of all these algorithms, the best possible algorithm will only be able to find a unique solution if there is an appropriate relationship between the measured k-ratios and the layer variables to be determined. If the best possible iterative algorithm is used and equation 1 gives accurate intensities with the correct specimen description, then if the iterative solution is ever going to be successful the iterative procedure must still be effective when the current estimates of unknown layer variables $T_i$ are very close to the true values $T0_i$. In this neighbourhood equation 1 can be linearized by considering small differences; that is, using a first order Taylor series expansion, the differences $(k_i-k0_i)$ are linear combinations of the small differences $(T_i-T0_i)$ where k0i are the measured k-ratios corresponding to the correct layer variables $T0_i$ and $k_i$ are the predicted k-ratios for $T_i$ from equation 1. Thus, the iterative procedure has to work out what combination of changes in $T_i$ are necessary to produce the change from $k_i$ to the give the measured $k0_i$. The effect of small changes can be determined by repetitive forward calculations using equation 1. If all the layer variables are initially set to their correct values, then the $k0_i$ can be computed. If one of the layer variables is altered by a small amount then running the forward calculation again will show what small changes, delta-$k_i$, are produced in each of the calculated k-ratios (i.e. delta-$k_i=k_i-k0_i$), If none of the k-ratios change substantially, then there is clearly no opportunity for determining the particular layer, variable by its effect on k-ratios. If at least some of the k-ratios change, then the change in the layer variable produces a "fingerprint" of changes delta-$k_i$ for each k-ratio. If this fingerprint happens to coincide with the fingerprint for one of the other layer variables then the changes in k-ratios produced by a positive change in one variable could be cancelled out by a suitable negative change in the other variable. In that case, there are an infinite number of combinations of values for these two variables that could explain the observed k-ratios and therefore there would be no way of deciding the correct values for these variables. The case where two "fingerprints" are similar is a simple example. In general, if it is possible to add up two or more linear combinations of fingerprints to produce a zero result. then the corresponding layer variable values cannot be uniquely determined. Thus, by using the forward calculation to explore the small neighbourhood of the ideal solution, it is possible to determine if there is no possibility of solution of the inverse problem.

In the case where the problem is soluble, then in the neighbourhood of the correct solution it is possible to find a combination of fingerprints for each layer variable that matches the observed delta-$k_i$. For example, this could be achieved by least squares fitting in which case the necessary changes in layer variables to take them to the correct values can be calculated as a linear sums of delta-$k_i$. In a real experiment, the measured $k_i$ will be subject to a number of measurement errors and these linear sums can be used to determine the effect of these errors on the determined layer variables. For example, if there are random errors in $k_i$, such as statistical fluctuations, the quadrature sum used in standard "propagation of errors" can be used whereas if there are systematic changes such as that produced by a change in beam current for example, the straightforward linear combination can be used to predict the effect on determined layer variables.

If this type of analysis is repeated for many analytical conditions, such as beam voltage, it is possible to discover all conditions where the problem is insoluble and for those conditions where it is soluble, establish to what extent errors in the measured k-ratios influence the accuracy and reproducibility of determined values for unknown layer variables.

If no conditions are found where the problem is "mathematically" soluble, then any iterative solution procedure will not be able to find a unique solution. When mathematical solution is found to be feasible and a set of optimum conditions are found, then the real iterative procedure can be tested for these optimum conditions by first simulating k-ratios from equation 1 for the correct specimen structure and then checking that, with these k-ratios as input, the procedure converges to the correct values $T0_i$ using starting guesses that are all different from $T0_i$. If convergence is not achieved, then this shows that there is room to improve the iteration solution procedure so that it can address the current analytical problem effectively.

There are therefore a number of different techniques that can be used to assess the feasibility of a proposed structure analysis process and it will also be appreciated that the use of mathematical techniques such as those described in relation to the series expansion for example may be used as an initial feasibility check after which a more detailed explanation procedure according to one of the other techniques may be used.

In most cases it is envisaged that the steps of the method (using appropriate models) will be performed upon a computer by the method being embodied within computer software ("computer-implemented"). Some such models will require powerful computers, particularly Monte Carlo techniques, in order to produce results with sufficient speed. Whilst the method may be performed upon a single computer such as that of an x-ray analysis system, it will be appreciated that different parts of the method could be performed upon different computers either independent of one another or, more preferably, linked over a network such as the Internet.

BRIEF DESCRIPTION OF THE DRAWINGS

Some examples of methods according to the invention are now described, with reference to the accompanying drawings, in which:—

DESCRIPTION OF EMBODIMENTS

A general overview is firstly provided according to one embodiment in terms of how the invention can advantageously provide a simulated experimental environment for exploring the capabilities of thin film software to solve a particular analysis problem. A software model is used to generate x-ray spectral data for a proposed sample and the data are analysed by "thin film analysis" software in order to determine whether the software is capable of deducing the structure of the sample by fitting certain "unknown" parameters.

Firstly a proposed sample is defined, this having the multilayered structure in the form of a thin film deposited upon a substrate. The specification for the sample is provided in terms of the approximate elemental composition, namely a composition typical of the sample to be analysed. This will in general be approximately the same as one of the unknowns that may be eventually analysed for real. The proposed sample is also defined in terms of the substrate and layers and the thicknesses of these layers. A first set of conditions is chosen, such as an electron beam energy, together with a beam current, x-ray detector parameters and an acquisition time. A typical x-ray spectrum that would be obtained from such a sample is then calculated from theory taking account of the characteristics of the x-ray detector and including suitable random number additions to simulate the effect of x-ray counting statistics. Further x-ray spectra are synthesised for other conditions, namely each incident beam voltage and measurement condition that is expected to be necessary. The synthesised x-ray spectra are then processed mathematically using the same algorithms that would be used on real spectra. These algorithms are typically used to subtract bremsstrahlung background and deal with the effects of spectral peak overlap to obtain a set of peak areas in counts and hence the peak intensities in counts per second. In addition the expected statistical standard deviation for each peak intensity may be calculated. The peak intensities are then converted into data suitable for input to the thin film analysis software program. This typically involves dividing the intensity by the value that would be obtained from a semi-infinite flat sample of pure element under the same excitation conditions. The pure element intensity is also determined by spectrum synthesis and the ratio is typically termed the "k-ratio" for that elemental line. Thus the "spectral data" are generated which represent that which would be generated by a sample in a real experiment.

The thin film analysis software for performing the calculation is then configured by selecting which elemental lines are to be used, which parameters of the real problem are unknown (that is thicknesses and/or composition values), which parameters are known and typical starting "guesses" are used for the unknown parameters to be fitted. The theoretical k-ratios for one set of conditions are then supplied as input data to the thin film analysis software which is then run in an attempt to find a solution by iteration that is consistent with the input k-ratios. If convergence is not achieved, different sets of conditions are tried and corresponding spectra synthesised to find a configuration that works. When convergence is achieved, the results for each estimated thickness and composition value are recorded.

A new set of theoretical k-ratios are then obtained. This can be achieved by repeating the whole spectrum synthesis procedure for each condition using a different set of random numbers to provide the effects of x-ray counting statistics. Alternatively, the calculated standard deviations for derived peak intensities can be used to generate suitable Gaussian-distributed random numbers that are used to perturb each k-ratio by a random amount consistent with the expected standard deviation of the corresponding peak intensity. Again, the set of k-ratios are used as input data to the thin film analysis software and the results for each estimated thickness and composition are recorded. This process effectively mimics a second experiment on the sample and the results will in general be different from the first experiment. By repeating the process many times (typically more than 100 times) the recorded results for each experiment show the variation in results that would be expected in practice when similar conditions are used. The mean and standard deviation for the results for the same parameter can then be calculated and provide an estimate of the precision that can be attained using a particular set of beam voltages and acquisition conditions.

By running many simulations, it is possible to check whether a quality control procedure could fail occasionally. If so, the configuration is modified until convergence is assured. With a fast computer, trial and error modification of the configuration is achieved more simply and faster than by doing live experiments on an instrument. Furthermore, the conditions can be optimised to find that set which gives the best precision on the results that can be achieved for a given total analysis time.

Potential measurement inaccuracy can also be taken into account in the simulation. For example, besides the variation due to x-ray counting statistics, the peak intensities may fluctuate from experiment to experiment because of variations in incident electron beam current. The likely percentage fluctuation in beam current can be added in quadrature to the fluctuation due to counting statistics to realistically represent these random excursions.

Systematic inaccuracies may be expected from spectrum processing (see for example, "Limitations to accuracy in extracting characteristic line intensities from x-ray spectra", P. J. Statham, J. Res. Natl. Inst. Stand. Technol. 107, 531-546 (2002)). X-ray spectrometers can often be calibrated to minimise these inaccuracies and for a given spectrometer and analysis problem it is often possible to estimate the worst case systematic error that could occur on a given peak area estimated by spectrum processing. If this error value is used in place of the estimated statistical standard deviation in the above procedure to randomly perturb the input k-ratio, the spread in results gives an estimate of the inaccuracies in determined thicknesses and concentrations that could result from errors in spectrum processing.

The invention thus provides a test bed for exploration to find a feasible set of conditions to use for real samples and gives a method for estimating the precision or reproducibiltiy of results caused by counting statistics and likely causes of fluctuation such as beam current. Furthermore, the test bed provides a method for estimating the likely consequences of inaccuracies involved in spectrum processing. Inaccuracies in the theoretical calculations within the thin film analysis software may still give systematic errors in the estimated thicknesses and concentrations. These systematic errors can usually be minimised by performing relative measurements using standards with known parameters.

Figure 3:
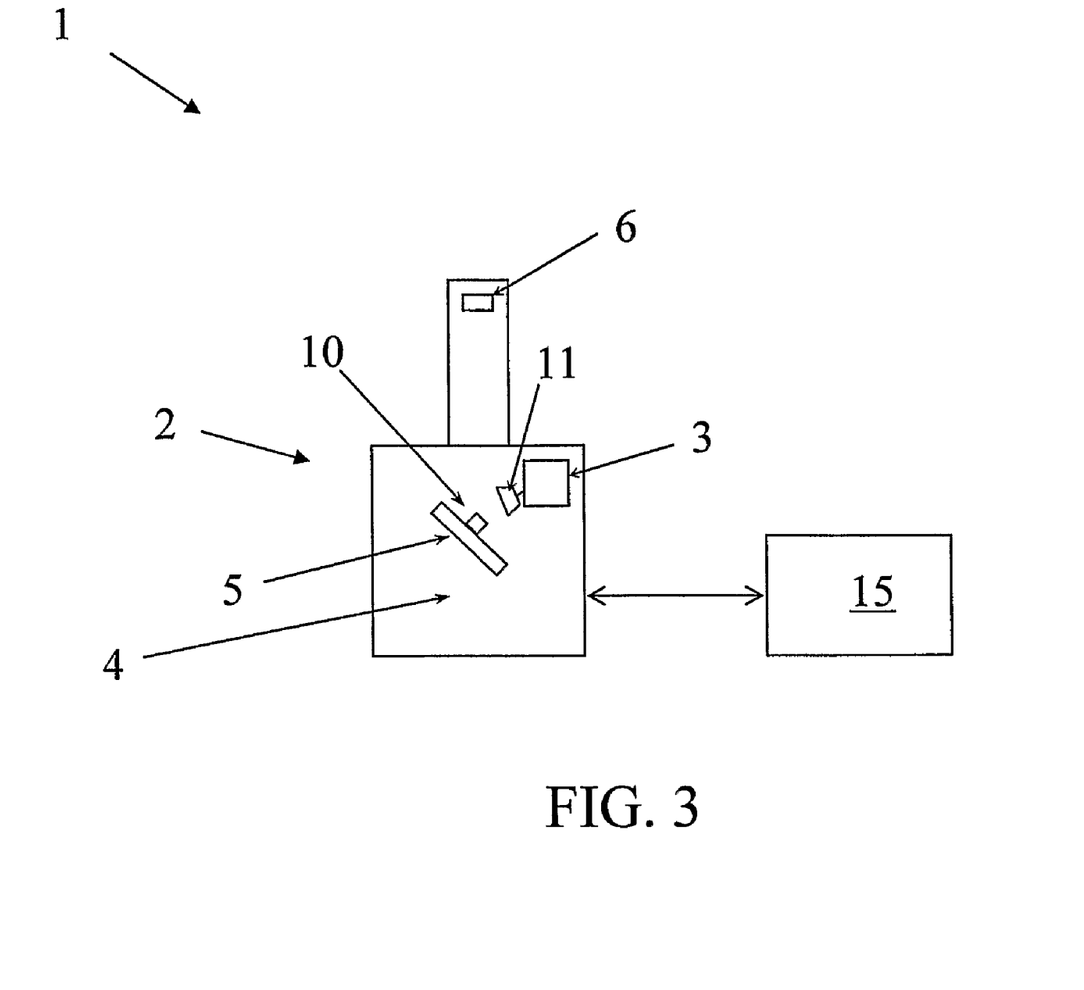
FIG. 3 is a schematic illustration of apparatus for performing a proposed structure analysis process.

An overview of a physical system 1 for performing a prior art structure analysis process of multi-layer samples (such as thin films) is shown in FIG. 3. The system comprises a scanning electron microscope (SEM) 2 having an x-ray analysis system 3, this being an INCA Energy x-ray analysis system (manufactured by Oxford Instruments Analytical Limited). The SEM has a chamber 4 containing a specimen holder 5 which can be tilted. An incident beam of electrons is emitted by an electron gun 6, this being focused upon a specimen 10 held within the specimen holder. Characteristic x-rays that are emitted as a result of the electron beam are detected by a detector 11 forming part of the x-ray analysis system 3. The SEM 2 includes a control computer 15 upon which software is executed to control the operation of the system 1. This computer can control the kV used to accelerate electrons from the electron gun 6 and thus alter the energy for the focused electron beam striking the specimen. To analyse the specimen 10, an electron beam energy and beam current is selected and an x-ray spectrum is acquired for a chosen acquisition time. Element peak intensities are obtained from the spectrum using a suitable method (for example "Deconvolution and background subtraction by least squares fitting with prefiltering of spectra", P J Statham, Anal. Chem. 49, 2149-2154, 1977 incorporated herein by reference). While the experimental conditions are stable, a known standard is moved under the beam into the same position occupied by the specimen 10 and a reference x-ray spectrum is obtained from the standard. The spectrum from the standard measurement is used to obtain the peak intensities that would be obtained from a flat sample of bulk pure element for each of the elements in the specimen to be analysed. Either a series of pure element or compound standards can be used, or a single standard can be used and the corresponding intensities worked out by applying calculated scaling factors to the appropriate standard measurement (see for example the operating manual for the thin film program "Stratagem" sold by SAMx, France). If necessary, the specimen and standard measurements are repeated at more incident beam energies.

A thin film analysis program (for example, "Stratagem" sold by SAMx, France) is then used to calculate the thicknesses and compositions of the various layers. To do this, the number of layers must be defined and any available information on substrate composition and composition of the various layers is supplied. Any unknown thicknesses and compositions will be determined by the program using the measured k-ratios for the elements involved at one or more beam energies. The k-ratio for each measured element is calculated and supplied as input to the thin film program which then attempts to find best fit parameters to the model by iteration. If the thin film program fails to converge, an error warning is given. Otherwise, the program gives a set of estimates for thicknesses and compositions for all the unknowns in the sample.

It will be appreciated that the above analysis process involves considerable experimental procedures which are costly particularly in terms of the time spent in determining whether a particular set of process conditions and parameters are feasible to use under all expected circumstances.

An example method of the invention is now described. In the invention, the SEM is not required and the method is used to discover and validate a preferred proposed method for analysis that can be used afterwards on the SEM with a real specimen.

Figure 4:
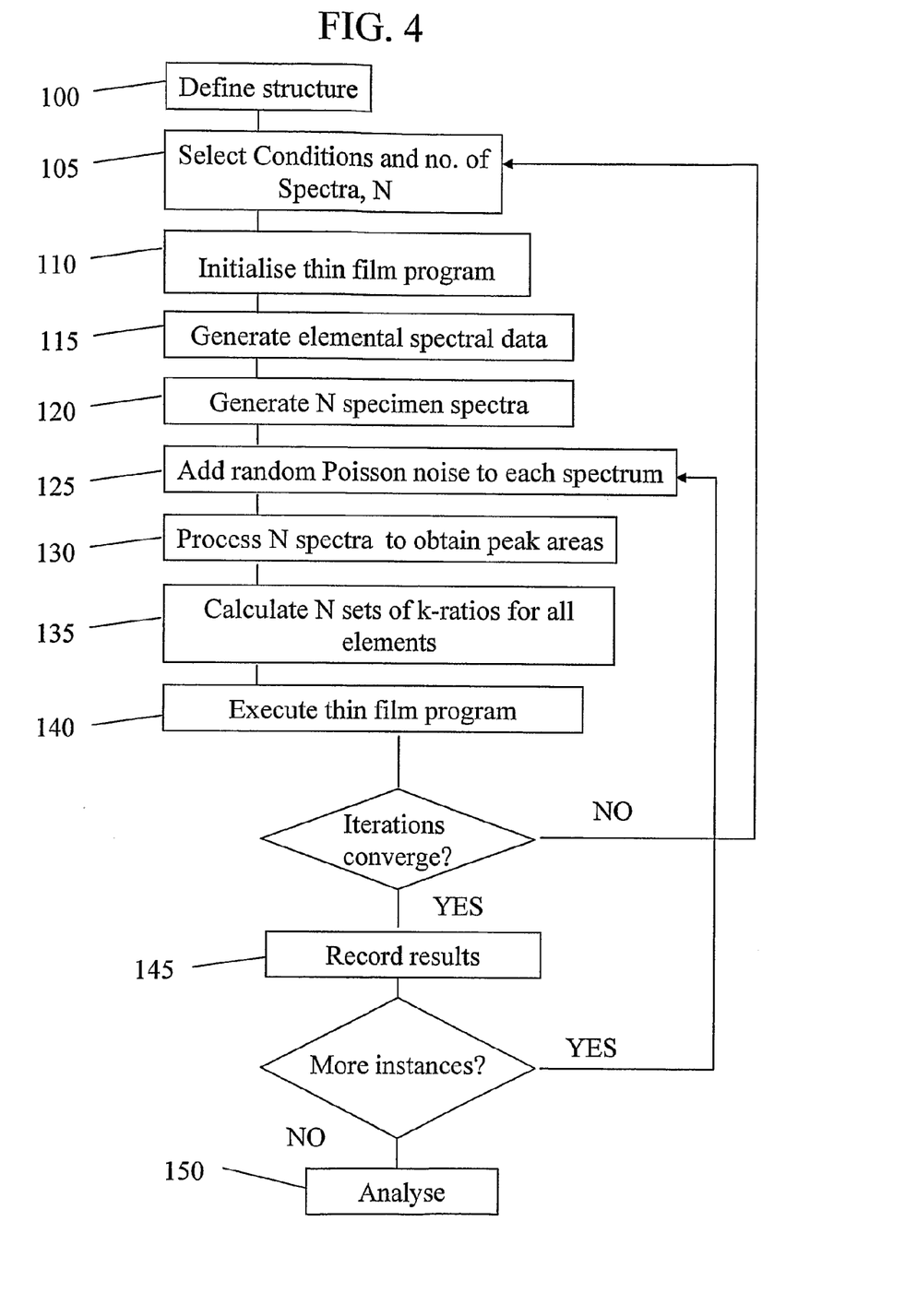
FIG. 4 is a flow diagram illustrating a first example method according to the invention; and, FIG. 5 is a flow diagram illustrating a second example method according to the invention.

Referring now to FIG. 4, the method begins at step 100 in which the structure of the multi-layered sample is defined in terms of parameters for use in the x-ray excitation model. Typical parameters include the number of layers, the thickness and density of each layer, the concentrations of each element in each layer and the concentrations in the substrate.

Then further details for each x-ray spectrum acquisition are defined at step 105, these relating to the experimental conditions. For example these include the incident beam energy for electrons (SEM kV), beam current, geometry of the sample (particularly take-off-angle for detected x-rays), total acquisition time and detector solid angle for collection of x-rays. One or more of different conditions are specified up to a total of NC, using these parameters.

Next a thin film program (the model for calculating the unknown fitted parameters), this being "Stratagem" in this example, is initialised according to the prior knowledge available (step 110). For each element present, a choice is made of which emission series to use for measurement (K, L or M). Where element concentrations or thicknesses and densities are known, these can be fixed so they do not change in the iterative solution process. Some elements may be combined in fixed proportions with others and these relationships can be used to enforce conditions that help the program to find a solution. For each condition where x-rays are recorded, a choice is made of which element series to measure to find k-ratios. Finally, "guesses" are assigned as starting parameters for the unknown thicknesses and concentrations that are to be estimated (fitted). To be a realistic test of what would happen with a real specimen, these starting parameters should be generic choices rather than exactly the same as for the typical specimen being simulated.

Note that the choice of a suitable set of conditions and the initialisation of the thin film program may be left to the skill of the operator. Alternatively, a computer algorithm could be used to make a suitable choice taking into account the physics of electron beam scattering and x-ray generation, the structure of the sample and the number of unknowns to be determined.

In step 115 a suitable prediction model is used to calculate the predicted x-ray spectrum data that would be obtained from flat homogeneous bulk samples of pure elements for the NC specified conditions. For electron beam excitation of a homogeneous bulk sample an accurate theoretical model has been achieved (see "Improved X-ray Spectrum Simulation for Electron Microprobe Analysis", Peter Duncumb, Ian R. Barkshire, Peter J. Statham, Microsc. Microanal. 7, 341-355, 2001). The method described in the abovementioned paper (which is incorporated herein by reference) is applied in this example. This model calculates the emitted spectral intensity and takes account of the efficiency of the detection system used to record the spectrum. Thus, the intensities for the selected emission series for pure bulk elements at the specified conditions are determined. In practice, the pure element intensities will be greater than those for the same elements in the multilayer specimen and longer acquisition times can be used for the reference pure element data so any statistical effects on the pure element measurements can be made negligible relative to those that effect the measurements of the specimen.

At step 120 a model is used to calculated the predicted x-ray spectrum data that would be obtained from the multilayer specimen for the NC specified conditions. The model used for prediction of bulk samples can be combined with existing models to predict intensity for multilayers on substrates (for example "Quantitative analysis of homogeneous or stratified microvolumes applying the model "PAP".", Pouchou, J. L. & Pichoir, F. (1991) In: Electron Probe Quantitation, Heinrich, K. F. J. & Newbury, D. E. (eds), Plenum Press, New York, 31-75 incorporated herein by reference).

In the present example, a hypothetical bulk sample spectrum is synthesised using the above theoretical model for bulk samples (implemented in the "INCA Energy" product, Oxford Instruments Analytical Limited). The element concentrations and beam current for this hypothetical spectrum are adjusted iteratively until the peak areas in the synthesised spectrum give the same k-ratios that are predicted by the thin film program "Stratagem" relative to pure element spectra taken at the specified beam current. Since, for a particular element both bremsstrahlung background intensity and peak intensity is approximately proportional to elemental concentration and film thickness, a simulated bulk spectrum with the same peak areas as a real spectrum will also exhibit a bremsstrahlung background that is similar to that which would be achieved in the real spectrum from a multi-layer specimen. This similarity ensures that statistical counting effects on the precision of background subtraction will be adequately modelled. Spectra are synthesised in this way for all NC conditions at step 120.

Each channel count in a real x-ray spectrum is subject to Poisson counting statistics. In the present example such Poisson counting statistics are modelled by the use of computer generated random numbers. An uncorrelated sequence of numbers is thereby generated and added to all the channels in each of the NC spectra (step 125).

Each spectrum is then processed at step 130 to remove background and correct for peak overlaps (a suitable technique is described in "Deconvolution and background subtraction by least squares fitting with prefiltering of spectra", P J Statham, Anal. Chem. 49, 2149-2154, 1977, incorporated herein by reference) to find the peak areas for the required element line series.

K-ratios are required for input to the "Stratagem" thin film program. The k-ratios are calculated by ratioing the calculated intensities with respect to those for the pure elements (step 135).

The thin film program is then executed using the input k-ratios to see if it can find a solution by iteration for all the unknown parameters (step 140) for each of the NC conditions. If it fails to converge, then a warning is given and the operator can select a new set of conditions and initialisation for the thin film (return to step 105).

If the iterations do converge, the results are saved (step 145) and a new "instance" is created by adding a new set of random numbers to give a new set of input data for each of the NC conditions. This "instance" represents another real experiment and when enough instances have been simulated, the overall standard deviation on the calculated results for all the instances can be determined in the analysis step 150.

Figure 5:
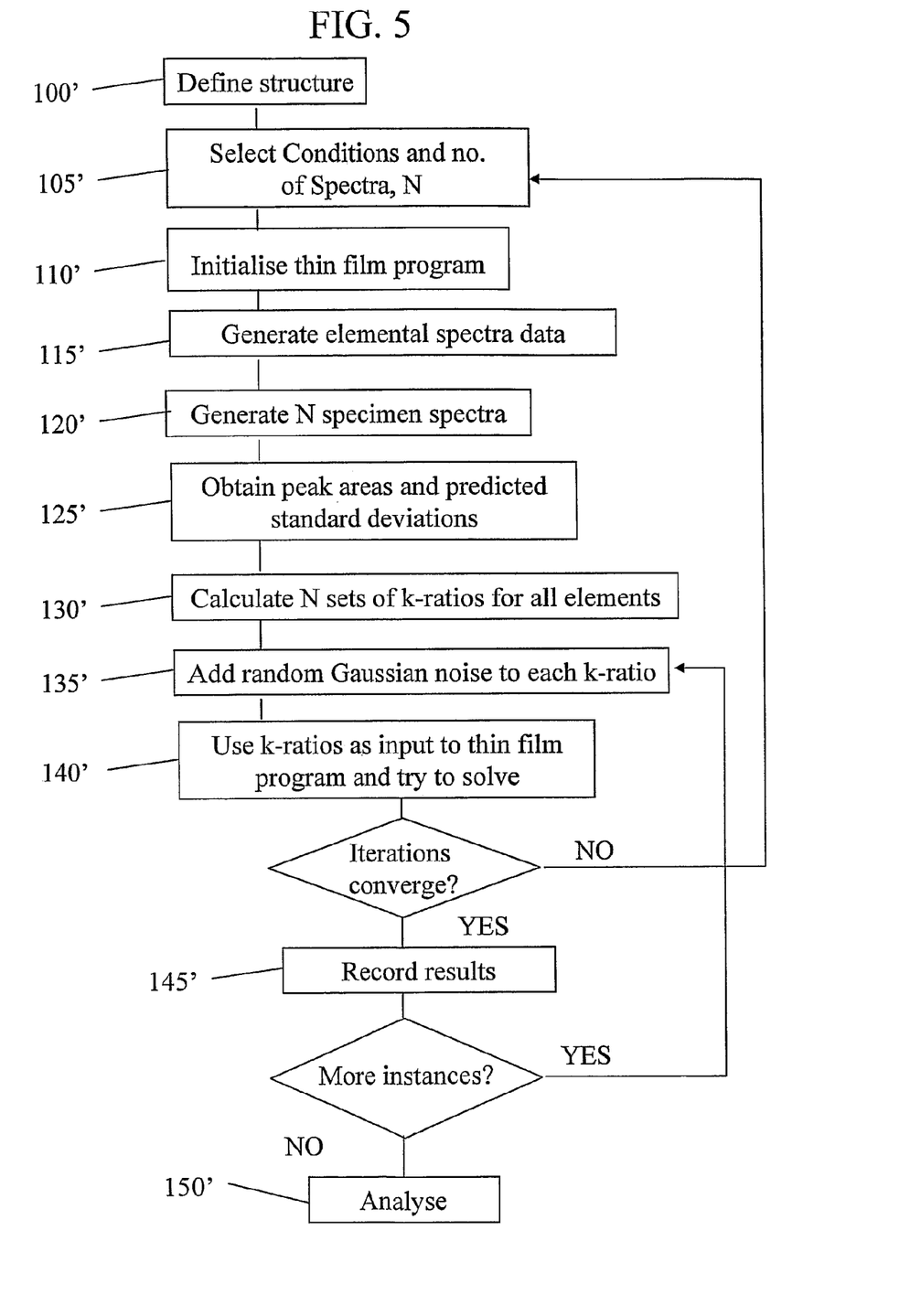

An alternative approach for simulating statistical variations, according to a second example method, is shown in FIG. 5. Primed reference numerals show steps analogous with FIG. 4. This involves mostly identical steps to those in FIG. 4 but there are two major differences. Firstly, in step 125', the method described in "Deconvolution and background subtraction by least squares fitting with prefiltering of spectra", P J Statham, Anal. Chem. 49, 2149-2154, 1977 (incorporated herein by reference), is used to predict the standard deviations for the peak areas determined by spectrum processing. Secondly, these standard deviations are used to modulate a random number generator to produce Gaussian distributed values for the k-ratios with the expected relative standard deviation (step 135'). The approach in FIG. 5 reduces the overall amount of computation and speeds up the calculation over many instances but does require one set of complicated calculations to predict the effect of spectrum processing on derived peak areas. The likely fractional fluctuation in beam current can be added in quadrature to the fluctuation in k-ratios due to counting statistics to represent this source of systematic error. Furthermore, systematic inaccuracies expected from spectrum processing can be estimated (see for example, "Limitations to accuracy in extracting characteristic line intensities from x-ray spectra", P. J. Statham, J. Res. Natl. Inst. Stand. Technol. 107, 531-546 (2002) incorporated herein by reference). These can be added as a random perturbation to the k-ratios to explore the effects of spectrum processing errors on the results obtained by the thin film analysis program.

In the methods of either of FIG. 4 or 5, if the iterations do not converge, this means that the problem cannot be solved by "inverting" the prediction of k-ratios from structure. It is possible that with a different set of measurements and conditions the problem could be solved and an operator with some experience can try modifying the configuration to see if another set of instances will be successful. It is important that the speed of calculation is sufficiently fast to enable this "trial and error" approach to make it interactive. Alternatively, a computer algorithm could be used to make successive changes automatically and discover what sets of conditions assure convergence.

Once the feasibility of solving the problem has been demonstrated, the conditions, number of measurements, acquisition times for x-ray spectra and initialisation of the thin film program can be adjusted to optimise the achievable precision for a given total measurement time.

Although the implementation of the invention has been described using x-ray spectra obtained with an energy-dispersive detection (EDS) system, this could equally well be achieved for measurements obtained with a wavelength-dispersive detection (WDS) system where a Bragg crystal monochromator and proportional counter detector is used to measure intensity from a specific element emission line. The key requirement is a method to simulate what would be achieved under real experimental conditions from a bulk specimen and this has already been demonstrated for WDS (for example, "X Ray Spectra simulation for WDS: Application to Electron Microprobe automation", C. FOURNIER, P. F. STAUB, C. MERLET, O. DUGNE, Microsc. Microanal. 7 (Suppl. 2), p 674 (2001) incorporated herein by reference). If the WDS intensity can be predicted for a particular element emission line on a bulk specimen, then the same technique as used for the EDS can be used to establish a hypothetical composition and a beam current value for a bulk specimen that would give the intensities and corresponding k-ratios that are predicted by the thin film program. In the case of WDS, the statistical calculations are considerably simpler because the higher energy resolution lessens the chance of peak overlap and background corrections are often negligible. Therefore, the relative standard deviation on measured k-ratios can be used in an approach similar to FIG. 5.

The thin film program "Stratagem" uses an approximation for the depth distribution of x-ray generation to enable a fast calculation of emitted intensities from the various layers. As the speed of computers is increasing, it is becoming possible to use more explicit models for x-ray generation such as a Monte Carlo simulation of electron scattering and ionisation (see for example, "The use of tracer experiments and Monte Carlo calculations in the phi(rho-z) determination of electron probe microanalysis", P. Karduck and W. Rehbach, (1991) In: Electron Probe Quantitation, Heinrich, K. F. J. & Newbury, D. E. (eds), Plenum Press, New York, 191-217 incorporated herein by reference). With such an explicit calculation method, the intensity can be predicted directly for a multi-layered specimen by using suitable cross sections for characteristic and bremsstrahlung radiation (for example see R. Gauvin and E. Lifshin (2002), "On the Simulation of True EDS X-Ray Spectra", Microscopy & Microanalysis, Vol. 8, Supp. 2, pp. 430-431, 2002, incorporated herein by reference). In this case, the spectrometer efficiency for either EDS or WDS is used to convert the calculated emission for a given beam current into a measured x-ray intensity. In the first instance, the Monte Carlo simulation is run to calculate intensities for the typical sample to find the k-ratios. After the addition of suitable perturbations representing statistical variation, an attempt is made to find a set of thicknesses and concentrations for the unknowns that is consistent with the input k-ratios. Although the Monte Carlo simulation process is quite different to the analytical depth distribution modelling used in "Stratagem", the method of iteratively modifying the "guesses" for unknowns can be identical to that used in "Stratagem". With each new guess, the Monte Carlo simulation is run to predict the intensities to see if they converge on a good fit to the input k-ratios.

In the above embodiments we have described a technique in which x-ray spectral data is generated using a model and the generated data are then inserted into a structure solver. As we have demonstrated, if the measured k-ratios are perturbed by small random amounts and a solution attempted by iteration, then both the capability of converging to a solution and the standard deviation on the determined result can be established by repeated simulations. This approach requires the capability to simulate spectra and multiple applications of the simulation in order to determine precision.

An alternative approach can be used that avoids the need to simulate spectra and reduces the need to perform large numbers of simulations in order to test the feasibility of the structure solver to converge for a given set of conditions. The thin film model can always predict k-ratios in the 'forward' direction as shown by equation 1 provided thicknesses and concentrations ("layer variables") are defined for all layers. If these k-ratios are provided as inputs to the structure solver and the starting values for the unknowns are set to the values corresponding to the hypothetical specimen, then equation 1 will predict k-ratios Identical to the starting values and the iteration will converge immediately. If just one of the k-ratios, $K_j$, is incremented by a small amount (say 1%) and the other k-ratios are unchanged, then when the iterative solution is attempted, the k-ratios will agree with equation 1 except for $K_j$. Provided the change in $K_j$ is sufficiently large, then the test for convergence will fail and the iterative procedure will have to perform an iteration and make an adjustment to the unknown values. This will change the prediction of k-ratios and may lead to further iterations. If the iterations fail to converge, then the problem is clearly unstable. However, if they do converge to a solution, then the change delta-$T_i$ from the ideal starting value for each unknown layer variable $T_i$ for a known change delta-$K_j$ in the jth k-ratio is recorded as $dT_i/dK_j$. This procedure is repeated for different $K_i$. If convergence is achieved for all $K_i$ then this suggests that the computer program can deal with this problem. If an estimate of the standard deviation, $\sigma_i$, in the measured $K_i$ is available, and the statistical fluctuations in all $K_i$ are independent, then the variance, $V_i$, in the calculated layer variable $T_i$ can be estimated as the sum of $((dT_i/dK_j)^2 \cdot \sigma_i^2)$ for all j. Systematic errors can occur in measured $K_i$. For example, if the beam current increases during the acquisition of an x-ray spectrum, then all $K_i$ derived from this spectrum will be increased in the same proportion. If an estimate of the systematic error, $e_i$, in the measure $K_i$ is available, then the error in the calculated variable $T_i$ can be estimated as the sum of $((dT_i/dK_j) \cdot e_j)$ for all j. A figure of merit can be computed for each source of error. For example, in the case of statistical errors, the maximum relative standard deviation in $T_i$, that is square root of $(V_i/T_i^2)$, gives the "worst case" relative error and a low value for this figure of merit would be desirable. Alternatively, the average relative error for all $T_i$ or the relative error for a specific layer variable can be chosen for the figure of merit. Similar figures of merit can be computed for errors due to systematic causes such as beam current variation.

Thus, if a typical specimen structure can be defined, then for one set of experimental conditions, in particular the beam energy, the possibility of solving the problem can be tested and one or more figures of merit can be computed to measure the effect of various potential sources of error on the results. If this procedure is repeated at several candidate experimental conditions, then the best set of conditions can be found that minimises the effect of one or more sources of error. If one source of error is likely to dominate, then the conditions that minimise the figure of merit for that error source is appropriate. Alternatively, if realistic values for, $\sigma_i$ and $e_i$ are available, then some combination of the related figures of merit can be used, such as the maximum of both figures of merit, to find the experimental conditions that are optimal.

If the feasibility of achieving convergence by the structure solver is all that is required, then a further method can be used. First, the true specimen structure is used to predict a set of k-ratios from equation 1 for all the NC conditions. These k-ratios are then used as input to the structure solver with a set of starting guesses for the unknown layer variables, $T0_j$, that are all slightly different from the true values. For example, these starting guesses could all be 1% greater than the true values or differences could be selected using a random number generator while still keeping the maximum relative difference to within a few %. The iterative structure solver is then started and it will attempt to adjust the unknown layer variables so that equation 1 predicts the k-ratios supplied as input for the NC different conditions. If convergence cannot be achieved, or the output values for any of the unknown layer variables are substantially different from the true values then this shows that it is not feasible to use this particular set of NC conditions for the structure analysis process so a new set of conditions needs to be tried.

In all the above approaches, the program that is used to find a solution by iteration may fail because it has limitations on its iteration procedure or uses an unsuitable algorithm. If iteration does fail, then it is not easy for the user to decide what is necessary to be changed in order to achieve a result. Furthermore, in order to establish feasibility it is necessary to run the structure solver routine which involves many iterations where at each iteration a full set of k-ratios have to be calculated by equation 1.

A more efficient method of establishing feasibility involves checking the mathematical behaviour of equation 1. By performing two calculations using equation 1 using first $T_j$ and then ($T_j$+delta-$T_j$) for layer variable j, the change delta-$k_i$ in k-ratio $k_i$ can be used to estimate the partial derivative ($\partial K_i/\partial T_j$)≈delta-$k_i$/delta-$T_j$. (If only the unknown variables are to be determined, the beam voltage $E_0$ and the known layer variables will remain fixed in equation 1) For the M k-ratios and N unknown layer variables, the M×N matrix of partial derivatives is the "Jacobian" for the model function in equation 1 with respect to the N unknown layer variables at a point in layer variable space. In the small neighbourhood of this point, the first order Taylor series expansion is thus described by the matrix equation $$J \times (T-T_0) = K - K_0 \quad \text{EQUATION 2}$$

where $K_0$ is the vector of k-ratios predicted by equation 1 for the particular point in layer variable space described by the particular layer variable values $T_0$, J is the M×N Jacobian evaluated at $T_0$, T is a vector of N layer variables, and K is the vector of M k-ratios predicted by equation 1 for layer variables T. At each step in the iterative procedure to solve equation 1, $T_0$ will be an estimate of the unknown layer variables and $K_0$ will be the predicted k-ratios for this estimate from equation 1. If the iterative procedure manages to get $K_0$ close to the measured k-ratios $K^m$ then the best estimate of T will be given by the solution of the equations shown in matrix form as $$J \times (T-T_0) = K^m - K_0 \quad \text{EQUATION 3}$$

If M>N there are more equations than unknowns and there is no unique solution in general. However, a "best fit" solution that minimises length of the residual vector, $$|J \times (T-T_0) - (K^m - K_0)|$$

can be found using singular value decomposition, SVD (see Numerical Recipes). SVD is used to factorise the M×N matrix J thus:

$$J = UWV^T$$

and then the best fit solution for T is given by $$T - T_0 = [VW^{-1}U^T](K^m - K_0) \quad \text{EQUATION 4}$$

or $$T - T_0 = P \times (K^m - K_0) \quad \text{EQUATION 5}$$

where P is sometimes called the "pseudo-inverse" of J. This procedure works provided there are at least N independent columns in the Jacobian. If there is a linear relationship between one or more columns, that reduces the number of independent columns. With less than N independent columns, it is no longer possible to find one unique best fit solution so the problem becomes insoluble. Linear relationships between columns therefore make the matrix J "ill conditioned" (Numerical Recipes). If the elements of the diagonal matrix W are taken in descending order, then the ratio of the Nth largest element to the largest element will be the "inverse condition number" (ICN) the reciprocal of the "condition number". If ICN=0, the Jacobian is "singular" and no solution is possible whereas with ICN=1, the matrix is perfectly conditioned. If the problem is ill conditioned then the results will be sensitive to small errors in computation or in the measured k-ratios. If ICN exceeds some threshold, say 0.1, then the iteration has a chance of converging successfully. If equation 4 cannot be solved when the iteration is close to the correct solution, then there is no way of solving equation 1 in general. Therefore, by evaluating ICN for different values of beam voltage, it is possible to find whether there is any beam voltage for which the problem can be solved by x-ray analysis using k-ratios.

The same principle can be applied if measurements of k-ratios are taken at more than one beam energy. For each $E_0$ the partial derivatives of the measured k-ratios are evaluated using the appropriate $E_0$ in equation 1 and added to the J matrix as additional rows. ICN is then evaluated at each combination of beam energies to find a combination where the problem is soluble. A multi-dimensional search will find at what combinations of beam energies the problem is soluble.

If there is no condition where equation 4 is soluble, then the only way to solve the problem is to remove the linear relationships between columns that are causing J to be ill conditioned. The layer variables involved can be identified using the SVD results (see for example, A. K. Bandyopadhyay et al, Int. J. Numer. Model. 2005; 18:413-427). Once identified, it may be possible to fix one or more of the unknown variables rather than leave them to be determined. The problem may then be mathematically soluble although the solution will now depend on the values chosen for the now fixed variables.

For conditions where equation 4 is soluble, then any fluctuations in $K^m$ will result in fluctuations in T as determined by equation 4. When the fluctuations in each $K^m_j$ are independent normal random deviates with standard deviation $\sigma_j$, the standard deviations for each layer variable $T_i$ in T is the square root of the sum of ($P_{ij}^2 \cdot \sigma_j^2$). for j=1 to M, where $P_{ij}$ is the matrix element in the N×M matrix P. This is a suitable method for finding the effect of errors due to counting statistics in the measured k-ratios When the fluctuations in each $K^m_j$ are correlated, as for example when beam current fluctuates during the measurement, then the error in $T_i$ will be the linear sum of $P_{ij} \cdot d_j$ for j=1 to M, where $d_j$ is the change in $K^m_j$ produced by the change in beam current. A similar calculation can be done to estimate the effect of systematic errors in spectrum processing; in this case, $d_j$ would be the error in $K^m_j$ involved in estimating the area of the peak in the x-ray spectrum. A figure of merit can be calculated for each source of error, for example, this could be the maximum relative error in TI or the mean square error in $T_i$. By plotting this figure of merit at each value of beam voltage, or at each combination of beam voltages where more than one condition is used, it is possible to decide on what condition or set of NC conditions that produces the best figure of merit. This effectively provides an expert system to help the inexperienced user to establish whether x-ray analysis can be used to solve the application problem and to find the best analytical conditions.

The invention finds particular application in electron beam excited x-ray analysis for layers between 1 and 100 nm in thickness, as occurs in semiconductor processes (metal and dielectric layers), magnetic thin films and catalytic chemistry for example.

The invention claimed is:

1. A method of determining the feasibility of a proposed structure analysis process, said process comprising electron beam excitation of x-rays from a multi-layered structure in order to determine the thicknesses and compositions of the layers, the method comprising:
  i) generating nominal x-ray data representing the x-ray excitation response of the multi-layered structure according to a first set of one or more process conditions, using nominal structure data comprising compositions and thicknesses for each layer;
  ii) analysing whether or not it is possible for a structure solver, when given the nominal x-ray data generated according to the first set of process conditions, to calculate output structure data comprising compositions and thicknesses for each layer; and
  iii) automatically repeating steps (i) and (ii) using different process conditions in place of the first set of process conditions so as to determine under which process conditions, if any, the proposed structure analysis process can be used to determine the thickness and composition of each layer in the multi-layered structure.

2. A method according to claim 1, wherein the nominal x-ray data are generated using a predictor model as a function of the elemental composition and layer thickness of each layer in the multi-layered structure.

3. A method according to claim 2, wherein the predictor model is used to generate nominal x-ray data representing the characteristic x-ray intensity response for a particular element within the multi-layered structure.

4. A method according to claim 2, wherein step (ii) comprises analysing the response of the predictor model to changes in the layer thicknesses and/or compositions within the nominal structure data.

5. A method according to claim 4, wherein the predictor model is analysed as an approximated series expansion.

6. A method according to claim 5, wherein the behaviour of the predictor model is represented as a matrix equation, wherein the nominal x-ray data output from the predictor model are represented as a vector of M values, wherein unknown layer thicknesses and/or compositions are represented as a vector of N variables, and wherein the partial derivatives relating the outputs to the layer thicknesses or compositions are represented as an M by N dimension Jacobian matrix.

7. A method according to claim 6, wherein the analysis is performed using an iterative technique to minimise the resultant residual vector.

8. A method according to claim 7, further comprising calculating a condition number representing the degree of solubility of the matrix equation for the layer thicknesses or compositions.

9. A method according to claim 8, wherein the condition number is compared with a threshold comprising a feasibility criterion.

10. A method according to claim 1, wherein, in step (ii), the nominal structure data is modified and input, together with the nominal x-ray data, into the structure solver adapted to iteratively calculate the composition and thickness of each layer of the multi-layered structure as output structure data using the nominal x-ray data and modified structure data.

11. A method according to claim 10, wherein, during operation, the structure solver calculates x-ray data for the modified structure data and compares the calculated x-ray data with the nominal x-ray data.

12. A method according to claim 11, wherein the effects of modifications to the nominal structure data are analysed by comparing the calculated x-ray data with the nominal x-ray data and comparing the results of the comparison with a feasibility criterion.

13. A method according to claim 12, wherein the feasibility criterion is met if a unique set of output structure data is found which produces corresponding x-ray data that is substantially identical to the nominal x-ray data and is substantially independent of the modifications applied to the nominal structure data.

14. A method according to claim 1, wherein, in step (ii), the x-ray data is modified and input, together with the nominal structure data, into a structure solver adapted to iteratively calculate the composition and thickness of each layer of the multi-layered structure using the modified x-ray data and nominal structure data, and to produce output structure data.

15. A method according to claim 14, wherein the effects of modifications to the x-ray data are analysed by comparing the output structure data with the nominal structure data in accordance with a feasibility criterion.

16. A method according to claim 15, wherein the feasibility criterion is met if, for every modification to the nominal x-ray data, the structure solver produces a unique set of output structure data having corresponding x-ray data that is substantially identical to the nominal x-ray data.

17. A method according to claim 1, wherein, using a Monte Carlo method, changes to nominal x-ray data generated from nominal structure data are produced by applying statistical distributions to the nominal x-ray data so as to produce a plurality of sets of modified x-ray data having a collective statistical distribution equivalent to that expected from performing the x-ray excitation experimentally.

18. A method according to claim 17, wherein in step (ii) each set of modified x-ray data is entered, together with the nominal structure data into an iterative structure solver for generating output structure data.

19. A method according to claim 18, wherein the process is deemed feasible if, for every modification to the nominal x-ray data, the structure solver produces a unique set of output structure data having corresponding x-ray data that is substantially identical to the nominal x-ray data.

20. A method according to claim 1, wherein step (i) comprises generating one or more sets of predicted spectral data, each set representing the x-ray excitation response of the structure according to a respective one of the said process conditions and wherein step (ii) comprises calculating output structure data for each set of process conditions, using each generated set of spectral data and nominal structure data.

21. A method according to claim 20, further comprising, for each set of process conditions, repeating step (i) a number of times so as to simulate the effects of Poisson counting statistics within each spectral data set by adding random numbers to the spectral data.

22. A method according to claim 20, wherein step (i) further comprises predicting a statistical distribution of x-ray peak areas due to Poisson counting statistics; and applying the statistical distribution to the spectral data.

23. A method according to claim 1, further comprising identifying sources of error within the analysis and assigning a figure of merit to the sensitivity of the analysis process to each source of error.

24. A method according to claim 23, further comprising repeating the method for each of a number of different process conditions in step (iii) and selecting a set of process conditions in which the figure of merit is minimised or is below a predetermined threshold.

25. A method according to claim 1, wherein each process condition comprises a different electron beam energy and/or a different detector geometry.

26. A method according to claim 1, wherein sets of x-ray data are generated for different processing conditions which represent fluctuations in the electron beam current.

27. A method according to claim 1, wherein the process conditions represent process variations associated with the use of predetermined apparatus for performing the electron beam excitation.

28. A method according to claim 1, wherein the nominal x-ray data are in the form of k-ratios.

29. A method according to claim 1, wherein initial values for the compositions and thicknesses of the layers in the nominal structure data are selected based upon known values or user inputted values.

30. A method according to claim 29, where a number of values for the composition and/or structure of the layers are fixed as a constant during the method.

31. A method according to claim 1, further comprises calculating a standard deviation for one or more values of the output structure data as a measure of achievable precision.

32. A method according to claim 1, wherein x-ray data are generated so as to represent data produced by an energy dispersive (EDS) or wavelength dispersive (WDS) system.

33. A method according to claim 1, wherein step (i) is performed using a computer software model of a physical electron beam x-ray analysis system.

34. A non-transitory computer program product comprising computer program code means adapted to perform the method of any of the preceding claims, when executed upon a computer.

35. A computer program product according to claim 34, embodied upon a non-transitory computer readable medium.

* * * * *